(12) United States Patent
Okada et al.

(10) Patent No.: US 10,617,667 B2
(45) Date of Patent: Apr. 14, 2020

(54) METHOD FOR TREATING BRAIN TUMORS

(71) Applicants: ONO PHARMACEUTICAL CO., LTD., Osaka-shi, Osaka (JP); The Regents of The University of California, Oakland, CA (US)

(72) Inventors: Hideho Okada, Mill Valley, CA (US); Tohru Kotani, Osaka (JP); Kazuhiko Takeda, Mishima-gun (JP)

(73) Assignees: ONO PHARMACEUTICAL CO., LTD., Osaka-shi, Osaka (JP); The Regents of The University of California, Oakland, CA (US)

( * ) Notice: Subject to any disclaimer, the term of this patent is extended or adjusted under 35 U.S.C. 154(b) by 0 days.

(21) Appl. No.: 16/176,361

(22) Filed: Oct. 31, 2018

(65) Prior Publication Data
US 2019/0125720 A1    May 2, 2019

Related U.S. Application Data

(60) Provisional application No. 62/580,059, filed on Nov. 1, 2017.

(51) Int. Cl.
| | |
|---|---|
| *A61K 31/353* | (2006.01) |
| *A61K 39/395* | (2006.01) |
| *A61P 35/00* | (2006.01) |
| *C07K 16/28* | (2006.01) |
| *A61K 39/00* | (2006.01) |

(52) U.S. Cl.
CPC ........ *A61K 31/353* (2013.01); *A61K 39/3955* (2013.01); *A61P 35/00* (2018.01); *C07K 16/2818* (2013.01); *A61K 2039/505* (2013.01); *A61K 2039/54* (2013.01)

(58) Field of Classification Search
CPC ...... A61K 31/353; A61K 39/395; A61P 35/00
See application file for complete search history.

(56) References Cited

U.S. PATENT DOCUMENTS

| | | | |
|---|---|---|---|
| 10,077,247 B2 * | 9/2018 | Asada | ............... C07D 405/14 |
| 2018/0002308 A1 | 1/2018 | Asada et al. | |

FOREIGN PATENT DOCUMENTS

| | | | |
|---|---|---|---|
| WO | 2006/121168 A1 | 11/2006 | |
| WO | 2016/111347 A1 | 7/2016 | |
| WO | WO-2016111347 A1 * | 7/2016 | ........ C07D 405/14 |
| WO | 2018/008711 A1 | 1/2018 | |

OTHER PUBLICATIONS

"Brain tumor", American Association of Neurological Surgeons downloaded Apr. 26, 2019.*
Horig et al. Journal of Translational Medicine 2004, 2(44), p. 1-6.*
Schafer et al. Drug Discovery Today, 2008, 13 (21/22), 913-916.*
Gary Kohanbash et al., "IMMU-42. ONO-AE3-208 Promotes Anti-Tumor Immune Activity and Survival in Glioma Models", Abstract of Neuro-Oncology, Nov. 6, 2017, vol. 19, Issue suppl_6, pp. vi122.
Tohm Kotani et al., "ONO-AE3-208 promotes anti-tumor immune activity and survival in glioma models", The 22nd Japanese Foundation for Cancer Research International Symposium on Cancer Chemotherapy published on Dec. 13-14, 2017, Poster Session p. 48.

* cited by examiner

*Primary Examiner* — Yong L Chu
(74) *Attorney, Agent, or Firm* — Sughrue Mion, PLLC

(57) ABSTRACT

Disclosed are a method for treating brain tumors, as well as a medicament for treating brain tumors. Provided is a medicament for treating brain tumors, the medicament containing a combination of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid or a pharmaceutically acceptable salt thereof, and an anti-PD-1 antibody. The combination exhibits an excellent effect for treating brain tumors, and is thus useful to treat brain tumors.

15 Claims, 1 Drawing Sheet
Specification includes a Sequence Listing.

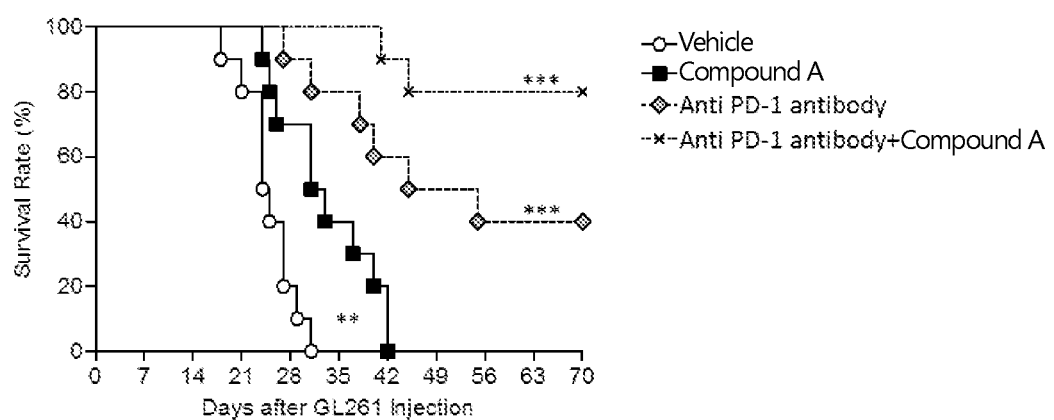

METHOD FOR TREATING BRAIN TUMORS

CROSS REFERENCE TO RELATED APPLICATIONS

This is an application claiming priority based on Provisional Patent Application No. 62/580,059 filed Nov. 1, 2017, the content of which is incorporated herein by reference in its entirety.

TECHNICAL FIELD

The present invention generally relates to a method for treating brain tumors, as well as a medicament for treating brain tumors.

BACKGROUND ART

Brain tumors occur in the skull, and include primary brain tumors and metastatic brain tumors. Primary brain tumors are tumors which originate in brain tissue, and metastatic brain tumors are tumors caused by metastasis of tumors formed in other organs to brain tissue. Primary brain tumors include benign tumors and malignant tumors.

Malignant primary brain tumors grow rapidly. Further, because this type of tumor infiltrates into brain tissue, it is hard to identify the border between the tumor and normal tissue, and it is difficult to completely remove the tumor cells by surgery. Accordingly, for highly malignant tumors, radiotherapy and chemotherapy are further used after surgery, in order to treat tumors that cannot be completely removed by surgery.

Benign primary brain tumors rarely grow rapidly; however, the internal volume of the skull is limited, and the intracranial pressure is thus accelerated due to the growth of the tumor, thereby causing headaches and nausea. Depending on the location of tumor, paralysis, dysbasia, speech disorder, dyskinesia, visual impairment, and like symptoms may occur.

Benign primary brain tumors generally have a clear border with normal tissue, and can be treated by surgical removal. However, fusion and infiltration of a tumor to surrounding important nerve tissue may occur depending on the tumor location, and such tumors cannot be completely removed, thereby leading to recurrence in some cases. When the tumor cannot be completely removed, radiation therapy is applied to prevent recurrence, as in the case of malignant tumors. Radiation therapy includes whole-brain radiotherapy and stereotactic radiotherapy. Whole-brain radiotherapy may lead to a development of dementia later in life. Compared with whole-brain radiotherapy, stereotactic radiotherapy may lead to a formation of new metastatic lesions. For infants, there is also a problem of intellectual underdevelopment caused by radiation therapy.

Metastatic brain tumors are treated by using removal surgery, radiation therapy, and chemotherapy, in combination, although it depends on the treatment protocol of the primary tumor.

Drugs currently used in chemotherapy include temozolomide, procarbazine, carmustine, nimustine, and ranimustine, which are alkylating agents, and bevacizumab, which is a vascularization inhibitor. However, these drugs are not satisfactory in their therapeutic effects, and more effective drugs are desired.

In order for brain tumor therapeutic agents to exhibit their effects, it is necessary to deliver the drug into the brain. For this purpose, the drug must penetrate the blood-brain barrier. If the drug cannot sufficiently be delivered to the brain, recurrence of the tumor may occur from tumor cells that cannot be removed by surgery. However, there is a restriction to a chemical structure of the drug; for example, it is required for the drug to have a small molecular weight to pass through the blood-brain barrier. This makes the development of brain tumor therapeutic agents difficult.

Cancer cells and cancer microenvironment have various immune checkpoint molecules that prevent immune responses against cancer. Immune checkpoint inhibitors have the action of inhibiting immune checkpoint molecules to block the immunosuppression mechanism, thereby activating immune responses against cancer. Accordingly, immune checkpoint inhibitors are used as therapeutic agents for cancer. As immune checkpoint inhibitors, nivolumab, pembrolizumab, etc., which are anti-PD-1 antibodies, have already been approved and available in the market in Japan and internationally.

Patent Document 1 teaches that Compound A (to be described later) strongly binds to an $EP_4$ receptor, and shows an antagonistic activity; however, Patent Document 1 does not describe or suggest effects of treating brain tumors.

CITED REFERENCE

Patent Document

Patent Document 1: WO2016/111347

DISCLOSURE OF THE INVENTION

Problems to be Solved by the Invention

An object of the present invention is to provide a method for treating brain tumors, as well as a medicament for treating brain tumors.

Means for Solving the Problems

In order to achieve the foregoing object, the present inventors conducted intensive studies, and consequently found that a combination of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid (hereinafter, simply referred to as "Compound A") or a pharmaceutically acceptable salt thereof, and an anti-PD-1 antibody (hereinafter, simply referred to as "the combination of embodiments of the present invention") was effective for the treatment of brain tumors. Further studies were carried out based on this finding. Thus, the present invention has been completed.

Specifically, the present invention relates to the followings:

[1] A medicament for treating a brain tumor, the medicament comprising a combination of Compound A or a pharmaceutically acceptable salt thereof, and an anti-PD-1 antibody.

[2] A medicament for treating a brain tumor, wherein Compound A or a pharmaceutically acceptable salt thereof, and an anti-PD-1 antibody are administered in combination.

[3] A medicament for treating a brain tumor, wherein Compound A or a pharmaceutically acceptable salt thereof, and an anti-PD-1 antibody are administered simultaneously or separately.

[4] The medicament according to any one of [1] to [3], wherein the brain tumor is a primary brain tumor.

[5] The medicament according to [4], wherein the primary brain tumor is glioma.

[6] The medicament according to any one of [1] to [5], wherein the anti-PD-1 antibody is intravenously or subcutaneously administered.

[7] The medicament according to any one of [1] to [6], wherein the anti-PD-1 antibody is nivolumab.

[8] A method for treating a brain tumor, the method comprising administering Compound A or a pharmaceutically acceptable salt thereof, and an anti-PD-1 antibody in combination to a subject in need thereof.

[9] A method for treating a brain tumor, the method comprising administering Compound A or a pharmaceutically acceptable salt thereof, in combination with an anti-PD-1 antibody to a subject in need thereof.

[10] A method for treating a brain tumor, the method comprising simultaneously or separately administering Compound A or a pharmaceutically acceptable salt thereof, and an anti-PD-1 antibody to a subject in need thereof.

[11] The method according to any one of [8] to [10], wherein the anti-PD-1 antibody is administered to the subject to whom Compound A or a pharmaceutically acceptable salt thereof was previously administered.

[12] The method according to any one of [8] to [10], wherein Compound A or a pharmaceutically acceptable salt thereof is administered to the subject to whom the anti-PD-1 antibody was previously administered.

[13] A method for treating a brain tumor, the method comprising administering an effective amount of an anti-PD-1 antibody to a subject in need thereof, the method further comprising administering an effective amount of Compound A or a pharmaceutically acceptable salt thereof.

[14] A method for treating a brain tumor, the method comprising administering an effective amount of Compound A or a pharmaceutically acceptable salt thereof to a subject in need thereof, the method further comprising administering an effective amount of an anti-PD-1 antibody.

[15] The method according to any one of [8] to [14], wherein the brain tumor is a primary brain tumor.

[16] The method according to [15], wherein the primary brain tumor is glioma.

[17] The method according to any one of [8] to [16], wherein the anti-PD-1 antibody is intravenously or subcutaneously administered.

[18] The method according to any one of [8] to [17], wherein the anti-PD-1 antibody is nivolumab.

[19] An agent for treating a brain tumor, the agent comprising an anti-PD-1 antibody, wherein the agent is used in combination with Compound A or a pharmaceutically acceptable salt thereof.

[20] The agent for treating a brain tumor according to [19], the agent comprising an anti-PD-1 antibody, wherein the agent is used in combination with Compound A or a pharmaceutically acceptable salt thereof, based on a package insert of an agent for treating a brain tumor, the agent comprising an anti-PD-1 antibody, and the package insert indicating that the agent can be used in combination with Compound A or a pharmaceutically acceptable salt thereof.

[21] An agent for treating a brain tumor, the agent comprising an anti-PD-1 antibody, wherein the agent is administered in combination with Compound A or a pharmaceutically acceptable salt thereof.

[22] An agent for treating a brain tumor, the agent comprising an anti-PD-1 antibody, wherein the agent is used in combination with Compound A or a pharmaceutically acceptable salt thereof, or the agent is used together with Compound A or a pharmaceutically acceptable salt thereof.

[23] An agent for treating a brain tumor, the agent comprising an anti-PD-1 antibody, wherein the agent is administered to a subject in need thereof to whom Compound A or a pharmaceutically acceptable salt thereof was previously administered.

[24] The agent according to any one of [19] to [23], wherein the brain tumor is a primary brain tumor.

[25] The agent according to [24], wherein the primary brain tumor is glioma.

[26] The agent according to any one of [19] to [25], wherein the anti-PD-1 antibody is intravenously or subcutaneously administered.

[27] The agent according to any one of [19] to [26], wherein the anti-PD-1 antibody is nivolumab.

[28] An agent for treating a brain tumor, the agent comprising Compound A or a pharmaceutically acceptable salt thereof, wherein the agent is used in combination with an anti-PD-1 antibody.

[29] The agent for treating a brain tumor according to [28], the agent comprising Compound A or a pharmaceutically acceptable salt thereof, wherein the agent is used in combination with an anti-PD-1 antibody, based on a package insert of an agent for treating a brain tumor, the agent comprising Compound A or a pharmaceutically acceptable salt thereof, and the package insert indicating that the agent can be used in combination with an anti-PD-1 antibody.

[30] An agent for treating a brain tumor, the agent comprising Compound A or a pharmaceutically acceptable salt thereof, wherein the agent is administered in combination with an anti-PD-1 antibody.

[31] An agent for treating a brain tumor, the agent comprising Compound A or a pharmaceutically acceptable salt thereof, wherein the agent is used in combination with an anti-PD-1 antibody, or the agent is used together with an anti-PD-1 antibody.

[32] An agent for treating a brain tumor, the agent comprising Compound A or a pharmaceutically acceptable salt thereof, wherein the agent is administered to a subject in need thereof to whom an anti-PD-1 antibody was previously administered.

[33] The agent according to any one of [28] to [32], wherein the brain tumor is a primary brain tumor.

[34] The agent according to [33], wherein the primary brain tumor is glioma.

[35] The agent according to any one of [28] to [34], wherein the anti-PD-1 antibody is intravenously or subcutaneously administered.

[36] The agent according to any one of [28] to [35], wherein the anti-PD-1 antibody is nivolumab.

[37] A combination of Compound A or a pharmaceutically acceptable salt thereof, and an anti-PD-1 antibody for producing a medicament for treating a brain tumor.

[38] A combination of Compound A or a pharmaceutically acceptable salt thereof, and an anti-PD-1 antibody for treating a brain tumor.

[39] Compound A or a pharmaceutically acceptable salt thereof for treating a brain tumor, wherein Compound A or a pharmaceutically acceptable salt thereof is administered in combination with an anti-PD-1 antibody.

[40] An anti-PD-1 antibody for treating a brain tumor, wherein the anti-PD-1 antibody is administered in combination with Compound A or a pharmaceutically acceptable salt thereof.

[41] Use of a combination of Compound A or a pharmaceutically acceptable salt thereof, and an anti-PD-1 antibody for producing a medicament for treating a brain tumor.

[42] Use of Compound A or a pharmaceutically acceptable salt thereof for producing an agent for treating a brain tumor, wherein the agent is administered in combination with an anti-PD-1 antibody.

[43] Use of an anti-PD-1 antibody for producing an agent for treating a brain tumor, wherein the agent is administered in combination with Compound A or a pharmaceutically acceptable salt thereof.

[44] A pharmaceutical composition for treating a brain tumor, the pharmaceutical composition comprising Compound A or a pharmaceutically acceptable salt thereof, and an anti-PD-1 antibody.

Effect of the Invention

The combination of embodiments of the present invention is useful to treat brain tumors.

BRIEF DESCRIPTION OF THE DRAWING

FIG. 1 shows effects of a combination of Compound A and an anti-mouse PD-1 antibody in mouse glioma cell line GL261 orthotopic-graft models using immunocompetent syngeneic C57BL/6 mice.

EMBODIMENTS FOR CARRYING OUT THE INVENTION

Embodiments of the present invention are described in detail below.

In one embodiment, there are provided a medicament for treating a brain tumor, the medicament comprising a combination of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid (Compound A) or a salt thereof, and an anti-PD-1 antibody; and a method for treating a brain tumor.

The medicament of the present invention is administered to a subject in need thereof, in particular to a patient suffering from a brain tumor.

Compound A is a compound having a chemical structure shown below, and has an $EP_4$ receptor-antagonistic action.

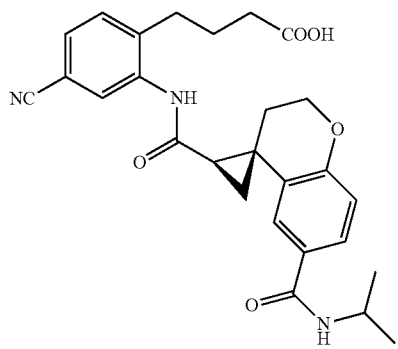

Compound A

As Compound A is a selective $EP_4$ antagonist, it has low toxicity and is excellent in safety.

The salt is preferably a pharmaceutically acceptable salt, and the salt is more preferably water-soluble. Examples of pharmaceutically acceptable salts include alkali metal salts, alkali-earth metal salts, ammonium salts, and amine salts. Examples of alkali metal salts include potassium salts and sodium salts. Examples of alkali-earth metal salts include calcium salts and magnesium salts. Examples of ammonium salts include tetramethylammonium salts. Examples of amine salts include salts of triethylamine, methylamine, dimethylamine, cyclopentylamine, benzylamine, phenethylamine, piperidine, monoethanolamine, diethanolamine, tris(hydroxymethyl)aminomethane, lysine, arginine, or N-methyl-D-glucamine.

Compound A and a salt thereof may be present in an unsolvated form, or a solvated form with a pharmaceutically acceptable solvent, such as water or ethanol. The solvate is preferably a hydrate. Compound A and a salt thereof may be transformed into a solvate by a known method.

Compound A may also be administered as a prodrug.

The prodrug as used herein refers to a compound that is transformed into Compound A in the body through reaction(s) with, for example, an enzyme and stomach acid. Examples of prodrugs of Compound A include Compounds A with a carboxy group that is esterificated or amidated (for example, Compounds A with a carboxy group that is ethylesterificated, phenylesterificated, carboxymethylesterificated, dimethylaminomethylesterificated, pivaloyloxymethylesterificated, 1-{(ethoxycarbonyl)oxy}ethylesterificated, phthalidylesterificated, (5-methyl-2-oxo-1,3-dioxolen-4-yl)methylesterificated, 1-{[(cyclohexyloxy)carbonyl]oxy}ethylesterificated, or methylamidated). These compounds may be produced by a method known per se. Moreover, the prodrug of Compound A may be a hydrate or a nonhydrate. The prodrug of Compound A may be one that transforms into Compound A under physiological conditions, such as described in Development of Drugs, Vol. 7, Molecular Design, pp. 163-198, 1990, Hirokawa Publishing Company.

Compound A may form a cocrystal together with an appropriate cocrystal former. The cocrystal is preferably a pharmaceutically acceptable cocrystal that is formed together with a pharmaceutically acceptable cocrystal former. The cocrystal is typically defined as a crystal that is formed of two or more different molecules by intermolecular interaction that is different from ionic bonding. Furthermore, the cocrystal may be a composite of a neutral molecule and a salt. The cocrystal can be prepared by a well-known method, such as melting crystallization, recrystallization with a solvent, or physical pulverization of the components together. Appropriate cocrystal formers include those described in WO2006/007448.

The atoms constituting Compound A may be replaced with their isotopes (for example, $^2H$, $^3H$, $^{13}C$, $^{14}C$, $^{15}N$, $^{16}N$, $^{17}O$, $^{18}O$, $^{18}F$, $^{35}S$, $^{36}Cl$, $^{77}Br$, and $^{125}I$).

Compound A, a salt thereof, a solvate thereof, or a prodrug thereof can be produced by a known method, for example, the method disclosed in Example 2-13 of Patent Document 1.

Compound A is generally formulated into preparations together with pharmaceutically acceptable excipients such as various additives and solvents, and the resulting preparations are administered as oral or parenteral preparations systemically or locally. The pharmaceutically acceptable excipients mean materials except active substances that are generally used for making pharmaceutical preparations. The pharmaceutically acceptable excipients are preferably excipients that are harmless, and do not show any pharmacological effect and do not inhibit the therapeutic effects of the active substances, at the dosage of the drug products. In addition, the pharmaceutically acceptable excipients can be used to enhance the effectiveness of the active substances and drug products, make the production of the drugs easy, improve drug stability, and improve easiness of drug use. Specifically, the material described in "*Iyakuhintenkabutujiten* 2016" (Yakujinippousha, 2016), (edited by International Pharmaceutical Excipients Council Japan)", etc. may be selected according to desired effects. Examples of the excipients include diluents or excipients, such as fillers, extenders, binders, moisturizers, disintegrators, surfactants, and lubricants.

Dosage forms for administration of Compound A include, for example, oral preparations (e.g., tablets, capsules, granules, powders, oral solutions, syrups, oral jelly agents, etc.), oro-mucosal preparations (e.g., tablets for oro-mucosal application, sprays for oro-mucosal application, semi-solid preparations for oro-mucosal application, gargles, etc.), preparations for injection (e.g., injections, etc.), preparations for dialysis (e.g., dialysis agents, etc.), preparations for inhalation (e.g., inhalations, etc.), preparations for ophthalmic application (e.g., ophthalmic liquids and solutions, ophthalmic ointments, etc.), preparations for otic application (e.g., ear preparation, etc.), preparations for nasal application (e.g., nasal preparations, etc.), preparations for recta (e.g., suppositories, semi-solid preparations for rectal application, enemas for rectal application, etc.), preparations for vaginal application (e.g., tablets for vaginal use, suppositories for vaginal use, etc.), and preparations for cutaneous application (e.g., solid preparations for cutaneous application, liquids and solutions for cutaneous application, sprays, ointments, creams, gels, patches, etc.). The administration route of the preparation comprising Compound A is not particularly limited. The preparation is administered by a method depending on various dosage forms, the age and sex of the patient, the conditions of the disease, and other conditions. For example, in the case of tablets, capsules, granules, etc., they are orally administered. In the case of injections, they can be administered intravenously, intramuscularly, or subcutaneously singly or in a mixture with a general replacement fluid, such as a physiological saline solution, a glucose solution, or an amino acid solution.

The dose of Compound A used in the combination of embodiments of the present invention varies depending on age, body weight, symptoms, therapeutic effects, administration route, treatment time, etc. In general, Compound A is orally administered once or several times a day at a dose of 1 ng to 1000 mg per time per adult, parenterally administered once or several times a day at a dose of 0.1 ng to 100 mg per time per adult, or intravenously administered continuously for 1 to 24 hours per day. Of course, because the dose varies depending on various conditions, as described above, an amount less than the above dose may be sufficient, or administration with a dose more than the above range may be necessary.

Examples of the anti-PD-1 antibody used in the combination of embodiments of the present invention include human anti-human PD-1 monoclonal (neutralizing) antibodies (e.g., nivolumab (OPDIVO (registered trademark)), Cemiplimab (REGN-2810), Sintilimab (IBI308), STI-A1110, GLS010 (AB122), and AGEN2034), humanized anti-human PD-1 monoclonal (neutralizing) antibodies (e.g., Pembrolizumab (KEYTRUDA (registered trademark), Spartalizumab (PDR-001), Tislelizumab (BGB-A317), AMP-514 (MEDI0680), ANB011 (TSR-042), JS001, Camrelizumab (SHR-1210), MGA012, CS1003, BAT-1306, and LZM009), and other antibodies (e.g., ENUM 244C8, AK105, and AK103).

Antibodies containing heavy- and light-chain complementarity-determining regions (CDRs) or variable regions (VRs) of the above known anti-PD-1 antibodies as well as antigen-binding fragments of the antibodies are also included in the scope of the anti-PD-1 antibody. For example, embodiments of the anti-PD-1 antibody or an antigen-binding fragment thereof include antibodies containing heavy- and light-chain complementarity-determining regions (CDRs) or variable regions (VRs) of nivolumab.

Therefore, the word "anti-PD-1 antibody" used herein is intended to encompass an anti-PD-1 antibody as well as an antibody fragment (antigen-binding fragment) that is capable of binding to PD-1. An antibody fragment or antigen-binding fragment is a single chain antibody, Fv, scFv, Fab, F(ab')2, Fab', scFv-Fc fragment, diabody, or any such fragment that has been stabilized such as by PEGylation.

Examples of antibodies or antigen-binding fragment thereof containing heavy and light chain complementarity-determining regions (CDRs) or variable regions (VRs) of nivolumab include:

(1) an anti-PD-1 antibody containing
  (a) a heavy-chain variable region CDR1 consisting of the amino acid sequence of SEQ ID NO: 3,
  (b) a heavy-chain variable region CDR2 consisting of the amino acid sequence of SEQ ID NO: 4,
  (c) a heavy-chain variable region CDR3 consisting of the amino acid sequence of SEQ ID NO: 5,
  (d) a light-chain variable region CDR1 consisting of the amino acid sequence of SEQ ID NO: 6,
  (e) a light-chain variable region CDR2 consisting of the amino acid sequence of SEQ ID NO: 7, and
  (f) a light-chain variable region CDR3 consisting of the amino acid sequence of SEQ ID NO: 8; and
(2) an anti-PD-1 antibody containing a heavy-chain variable region consisting of the amino acid sequence of SEQ ID NO: 1, and a light-chain variable region consisting of the amino acid sequence of SEQ ID NO: 2 (preferably an isolated human monoclonal IgG4 antibody of (1) or (2)).

The anti-PD-1 antibody used in the combination of embodiments of the present invention is preferably an antibody containing heavy- and light-chain complementarity-determining regions (CDRs) or variable regions (VRs) of nivolumab (including nivolumab), and more preferably nivolumab.

The anti-PD-1 antibody is generally formulated into preparations together with pharmaceutically acceptable excipients such as various additives and solvents, and the resulting preparations are administered systemically or locally.

Examples of the dosage form used for the administration of the anti-PD-1 antibody include preparations for injections (e.g., injections). In general, they can be administered intravenously, intramuscularly, or subcutaneously singly or in a mixture with a general replacement fluid, such as a physiological saline solution, a glucose solution, or an amino acid solution.

In the present invention, one or any combination of anti-PD-1 antibodies can used in combination with Compound A or a pharmaceutically acceptable salt thereof.

The dose of the anti-PD-1 antibody used in the combination of embodiments of the present invention varies depending on age, body weight, symptoms, therapeutic effects, administration route, treatment time, etc., and is adjusted so that the optimal desired effect is achieved. The dose of the anti-PD-1 antibody in one embodiment is 0.1 to 20 mg/kg body weight. For example, when nivolumab is used, the dose thereof in one embodiment is 0.3 to 10 mg/kg body weight, preferably 1 mg/kg, 2 mg/kg, 3 mg/kg, or 6 mg/kg body weight per time. The dose thereof in another embodiment is 80 mg, 240 mg, or 480 mg per time. The above dose is generally administrated every two weeks, three weeks, or four weeks.

In a preferable embodiment of administration of a combination of Compound A and nivolumab, nivolumab is administered by intravenous drip infusion at a dose of 240 mg per time every two weeks or at a dose of 480 mg per time every four weeks, and Compound A is orally administered once a day at a dose of 1 to 100 mg, and preferably 5 to 20 mg.

In another preferable embodiment of administration of a combination of Compound A and nivolumab, nivolumab is administered by intravenous drip infusion at a dose of 1 mg/kg body weight per time every three weeks, 2 mg/kg body weight per time every three weeks, or 3 mg/kg body weight per time every two weeks; and Compound A is orally administered once a day at a dose of 1 to 100 mg, and preferably 5 to 20 mg.

Moreover, in another embodiment of administration of nivolumab when Compound A and nivolumab are administered in combination, nivolumab is administered four times by intravenous drip infusion at a dose of 1 mg/kg body weight per time every three weeks; then nivolumab is administered by intravenous drip infusion at a dose of 3 mg/kg body weight per time every two weeks, or administered four times by intravenous drip infusion at a dose of 80 mg per time every three weeks; and then nivolumab is administered by intravenous drip infusion at a dose of 240 mg per time every two weeks. In some cases, nivolumab is administered four times by intravenous drip infusion at a dose of 240 mg per time every three weeks, and then administered by intravenous drip infusion at a dose of 240 mg per time every two weeks.

The combination of embodiments of the present invention is useful for the treatment of brain tumors. Brain tumors are tumors occurring inside the skull, and include primary brain tumors and metastatic brain tumors. Primary brain tumors include benign tumors and malignant tumors. Specific examples include, but are not limited to, glioma, schwannoma, acoustic tumor, medulloblastoma, central nervous system malignant lymphoma, intracranial germ cell tumor, atypical meningioma, pineoblastoma, primary central nervous system malignant lymphoma, pituitary adenoma, meningioma, pilocytic astrocytoma, craniopharyngioma, choroid-plexus tumor, ependymoma, pituitary carcinoma, and the like. Glioma includes pilocytic astrocytoma, diffuse astrocytoma, oligodendroglioma, oligoastrocytoma, anaplastic astrocytoma, anaplastic oligodendroglioma, anaplastic oligoastrocytoma, and glioblastoma. Metastatic brain tumors refer to tumors caused by metastasis of primary tumors, such as lung cancer, breast cancer, rectal cancer, renal cancer, bladder cancer, gastric cancer, head and neck cancer, hepatic cancer, colorectal cancer, and uterine cancer, to the brain.

The combined administration of the combination of embodiments of the present invention has a therapeutic effect for brain tumors significantly higher than that of single administration of each drug.

The combination of embodiments of the present invention can thereby exhibit the maximum therapeutic effect for brain tumor patients for whom the therapeutic effect of a single use of an anti-PD-1 antibody or Compound A is not sufficient for treating their brain tumors. Moreover, the combination of embodiments of the present invention makes it possible to administer each drug with a lower dose, and can be expected to reduce side effects. Even if the dose of each drug is less than the effective amount thereof in the case of single administration, the therapeutic effect can be exhibited by administering them in combination.

The dose of each of the anti-PD-1 antibody and Compound A in the combination of the present invention is preferably an amount (effective amount) in which therapeutic effects for brain tumors can be exhibited when they are administered in combination.

The combination of the present invention in one embodiment suppresses (prevents or delays) recurrence of a brain tumor.

In embodiments of the present invention, the treatment of a brain tumor means that at least one of the following changes occurs: a reduction of the brain tumor size, suppression (delay or arrest) of brain tumor growth, suppression (delay or arrest) of brain tumor metastasis, suppression (prevention or delay) of recurrence of a brain tumor, relief of one or more symptoms related to brain tumors, and an improvement in the survival rate of mammals (preferably human patients) in need of the treatment of brain tumors.

The combined administration of the combination of embodiments of the present invention comprises simultaneous or separate administration (e.g., successive administration) of the anti-PD-1 antibody and Compound A in the same or different dosage forms.

The simultaneous administration of the combination of the present invention means administration of two or more therapeutic agents in such a manner that the administration of each therapeutic agent at least partially overlaps temporally.

The separate administration of the combination of the present invention means administration of two or more therapeutic agents in such a manner that the administration of each therapeutic agent does not overlap temporally.

The combined administration of the combination of embodiments of the present invention comprises an administration of effective amounts of the anti-PD-1 antibody and Compound A to a mammal (preferably a human patient).

The combined administration of the combination of embodiments of the present invention comprises administering a brain tumor therapeutic agent comprising Compound A in combination with (together with) the anti-PD-1 antibody, and administering a brain tumor therapeutic agent comprising the anti-PD-1 antibody in combination with (together with) Compound A.

The combined administration of the combination of embodiments of the present invention comprises a method for administering Compound A to a patient to whom the anti-PD-1 antibody has been administered prior to the administration of Compound A, and a method for administering the anti-PD-1 antibody to a patient to whom Compound A has been administered prior to the administration of the anti-PD-1 antibody.

The combined administration of the combination of embodiments of the present invention includes a combined administration based on the instructions of the package insert of a brain tumor therapeutic agent comprising Compound A, the package insert indicating that the agent can be used in combination with the anti-PD-1 antibody; and a combined administration based on the instruction of the package insert of a brain tumor therapeutic agent comprising the anti-PD-1 antibody, the package insert indicating that the agent can be used in combination with Compound A. The instructions of the package insert include, for example, instructions regarding efficacy and effects, instructions regarding usage and dosage, and the like.

The combination of embodiments of the present invention may be further used in combination with other drugs, in order to (1) supplement and/or enhance the therapeutic effects, (2) improve kinetics and absorption, and reduce the dose, and/or (3) reduce side effects. Examples of other drugs include malignant glioma therapeutic agents, such as alkylating agents (e.g., temozolomide, procarbazine, carmustine, nimustine, and ranimustine) and vascularization inhibitors (e.g., bevacizumab).

The combination of embodiments of the present invention has low toxicity and thus can be safely used as medicaments.

In the present specification, the meaning of the terms "comprise" and "contain" includes the concept of the terms "consist of" and "consist essentially of."

Unless otherwise defined, all technical and scientific terms, and all abbreviations used in this specification have the meaning as normally understood by a skilled person in the art to which the present invention pertains. The contents of the all patent documents, non-patent documents, and reference documents explicitly cited herein are incorporated herein as a part of the specification.

EXAMPLES

Embodiments of the present invention are described below in greater detail. It is to be noted that embodiments of the present invention are not limited by the following descriptions.

Production Example

According to the description in Example 2-13 of Patent Document 1, 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid (Compound A) was produced.

Pharmacological Experiment Example

Effects of Combination of Compound A and an Anti-Mouse PD-1 Antibody in Mouse Glioma Cell Line GL261 Orthotopic-Graft Models Using Immunocompetent Syngeneic C57BL/6 Mice The effect of a combination of Compound A and an anti-mouse PD-1 antibody (4H2, see WO2006/121168) was evaluated in mouse glioma cell line GL261 orthotopic-graft models using immunocompetent syngeneic C57BL/6 mice. GL261 was cultured in a $CO_2$ incubator using an RPMI medium (Mediatech, Inc.) containing 10 vol % of FBS, 100 units/mL of penicillin, and 100 µg/mL of streptomycin. On the day of transplant, GL261 was harvested after removing the culture supernatant, and washing the cells with PBS. The harvested GL261 cells were suspended in PBS to obtain transplant cells. The transplant cells ($5 \times 10^4$) were then transplanted to the brain of female C57BL/6J mice (The Jackson Laboratory) under anesthesia.

After 5 days from transplant, the mice were divided into 4 groups: a vehicle group, a Compound A single group, an anti-mouse PD-1 antibody single group, and a combination group (Compound A and the anti-mouse PD-1 antibody). Each group included 10 mice. Compound A was orally administered at a 3 mg/kg dose to the mice of the Compound A single group and the combination group one time after 5 days from transplant, and then twice a day after 6 to 70 days from transplant. The anti-mouse PD-1 antibody was intraperitoneally administered to the mice of the anti-mouse PD-1 antibody single group and the combination group at a dose of 20 mg/kg after 5 days from transplant, and at a dose of 10 mg/kg after 11, 17, 23, 29, 35, 41, 47, 53, 59, and 65 days from transplant. Distilled water was orally administered to the mice of the vehicle group and the anti-mouse PD-1 antibody single group whenever Compound A was administered to the Compound A single group and the combination group. Further, a mouse IgG antibody was intraperitoneally administered to the mice of the vehicle group and the Compound A single group whenever the anti-mouse PD-1 antibody was administered to the anti-mouse PD-1 antibody single group and the combination group. The general condition of the mice was observed once a day from the day following the day of transplant of GL261, and scored according to the following table. Thus, the survival rate of the mice was evaluated.

TABLE 1

| Parameter | Symptom | Score |
|---|---|---|
| Appearance etc. | No abnormalities | 0 |
| | Pallor of extremities (anemia-like symptoms) | 1 |
| | Disheveled fur | 1 |
| | Hunting | 1 |
| | Weight loss (>15%) | 3 |
| Behavior | No abnormalities | 0 |
| | Decrease in locomotor activity (mild) | 1 |
| | Decrease in locomotor activity (severe) | 3 |
| Respiratory condition | No abnormalities | 0 |
| | Abnormalities occurred (e.g., bradypnea) | 2 |

Mice that showed a score of 5 were euthanized. Further, mice that satisfied any one of the following conditions were euthanized, regardless of their scores.

When the mice showed the symptoms listed in the above table, and also lost weight 20% or more.

When the mice had difficulty breathing.

When the mice walked with unsteady gait.

When the mice showed paralysis.

FIG. 1 shows the evaluation results of the survival rate of the mice. The results in FIG. 1 show that all the mice in the vehicle administration group had died after 31 days. In the Compound A single administration group, the survival time was longer than that of the vehicle administration group; however, all the mice had died after 42 days. In the administration of the anti-PD-1 antibody alone, the survival rate was improved, and the median survival time was 50 days. Furthermore, due to the combined use of the anti-PD-1 antibody and Compound A, the survival rate after 50 days, which was the median survival time of the anti-PD-1 antibody single administration group, was 80%, and the median survival time of the combination group was 70 days or more. The score showing the general condition of the mice survived after 70 days was 0, and their health conditions were good.

The above results indicate that the combined administration of the anti-PD-1 antibody and Compound A exhibited synergistic effects in the brain tumor models with tumors transplanted in the brain, and the survival rate was significantly improved, as compared with single administration of each drug. Therefore, the combination of the anti-PD-1 antibody and Compound A is considered to be useful as a medicament for treating brain tumors.

INDUSTRIAL APPLICABILITY

The combination of the present invention has an excellent effect for treating brain tumors, and is thus useful as a medicament for treating brain tumors.

The invention claimed is:

1. A method for treating a glioma, the method comprising simultaneously or separately administering an effective amount of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid or a pharmaceutically acceptable salt thereof, and an effective amount of an anti-PD-1 antibody to a subject in need thereof.

2. The method according to claim 1, wherein the anti-PD-1 antibody is administered to the subject to whom the 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid or a pharmaceutically acceptable salt thereof was previously administered.

3. The method according to claim 1, wherein the 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid or a pharmaceutically acceptable salt thereof is administered to the subject to whom the anti-PD-1 antibody was previously administered.

4. A method for treating a glioma, the method comprising administering an effective amount of an anti-PD-1 antibody to a subject in need thereof, the method further comprising administering an effective amount of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid or a pharmaceutically acceptable salt thereof.

5. A method for treating a glioma, the method comprising administering an effective amount of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid or a pharmaceutically acceptable salt thereof to a subject in need thereof, the method further comprising administering an effective amount of an anti-PD-1 antibody.

6. The method according to claim 1, wherein the anti-PD-1 antibody is intravenously or subcutaneously administered.

7. The method according to claim 1, wherein the anti-PD-1 antibody is nivolumab.

8. The method according to claim 2, wherein the anti-PD-1 antibody is intravenously or subcutaneously administered.

9. The method according to claim 2, wherein the anti-PD-1 antibody is nivolumab.

10. The method according to claim 3, wherein the anti-PD-1 antibody is intravenously or subcutaneously administered.

11. The method according to claim 3, wherein the anti-PD-1 antibody is nivolumab.

12. The method according to claim 4, wherein the anti-PD-1 antibody is intravenously or subcutaneously administered.

13. The method according to claim 4, wherein the anti-PD-1 antibody is nivolumab.

14. The method according to claim 5, wherein the anti-PD-1 antibody is intravenously or subcutaneously administered.

15. The method according to claim 5, wherein the anti-PD-1 antibody is nivolumab.

* * * * *

SEQUENCE LISTING

<160> NUMBER OF SEQ ID NOS: 8

<210> SEQ ID NO 1
<211> LENGTH: 113
<212> TYPE: PRT
<213> ORGANISM: Homo sapiens

<400> SEQUENCE: 1

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 2
<211> LENGTH: 107
<212> TYPE: PRT
<213> ORGANISM: Homo sapiens

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 3
<211> LENGTH: 5
<212> TYPE: PRT
<213> ORGANISM: Homo sapiens

<400> SEQUENCE: 3

Asn Ser Gly Met His
1               5

<210> SEQ ID NO 4
<211> LENGTH: 17
<212> TYPE: PRT
<213> ORGANISM: Homo sapiens

```
<400> SEQUENCE: 4

Val Ile Trp Tyr Asp Gly Ser Lys Arg Tyr Tyr Ala Asp Ser Val Lys
1               5                   10                  15
Gly

<210> SEQ ID NO 5
<211> LENGTH: 4
<212> TYPE: PRT
<213> ORGANISM: Homo sapiens

<400> SEQUENCE: 5

Asn Asp Asp Tyr
1

<210> SEQ ID NO 6
<211> LENGTH: 11
<212> TYPE: PRT
<213> ORGANISM: Homo sapiens

<400> SEQUENCE: 6

Arg Ala Ser Gln Ser Val Ser Ser Tyr Leu Ala
1               5                   10

<210> SEQ ID NO 7
<211> LENGTH: 7
<212> TYPE: PRT
<213> ORGANISM: Homo sapiens

<400> SEQUENCE: 7

Asp Ala Ser Asn Arg Ala Thr
1               5

<210> SEQ ID NO 8
<211> LENGTH: 9
<212> TYPE: PRT
<213> ORGANISM: Homo sapiens

<400> SEQUENCE: 8

Gln Gln Ser Ser Asn Trp Pro Arg Thr
1               5
```